United States Patent
Böss et al.

(10) Patent No.: US 7,022,709 B2
(45) Date of Patent: Apr. 4, 2006

(54) SELECTIVE PDE 2 INHIBITORS AS PHARMACEUTICALS FOR IMPROVING PERCEPTION

(76) Inventors: Frank-Gerhard Böss, Auf dem Scheidt 29f, 42115 Wuppertal (DE); Martin Hendrix, Wolfskaul 8, 51061 Köln (DE); Gerhard König, Burgmüllerstr.47, 40235 Düsseldorf (DE); Ulrich Niewöhner, Gartenstr.3, 42929 Wermelskirchen (DE); Karl-Heinz Schlemmer, Wildsteig 22 a, 42113 Wuppertal (DE); Rudy Schreiber, 555 W. Middlefield Rd., Mountain View, CA (US) 94043; Franz-Josef Van Der Staay, Matthias-Claudius-Weg 15 a, 53797 Lohmar (DE); Dagmar Schauss, Stackenbergstr. 15, 42329 Wuppertal (DE)

( * ) Notice: Subject to any disclaimer, the term of this patent is extended or adjusted under 35 U.S.C. 154(b) by 0 days.

(21) Appl. No.: 09/911,277

(22) Filed: Jul. 23, 2001

(65) Prior Publication Data

US 2002/0132754 A1  Sep. 19, 2002

(30) Foreign Application Priority Data

Aug. 1, 2000 (DE) .............................. 100 37 411
May 11, 2001 (DE) .............................. 101 22 893

(51) Int. Cl.
*A61K 31/519* (2006.01)
(52) U.S. Cl. .................................. 514/262.1
(58) Field of Classification Search ............... 514/262, 514/262.1
See application file for complete search history.

(56) References Cited

U.S. PATENT DOCUMENTS 5,141,936 A * 8/1992 Rupp et al.
6,174,884 B1 * 1/2001 Haning et al.

FOREIGN PATENT DOCUMENTS

| EP | 0771799 | 5/1997 |
| WO | 9840384 | 9/1998 |
| WO | WO 98/40384 | * 9/1998 |

OTHER PUBLICATIONS

Merriam-Webster's Collegiate Dictionary, 10th edition, 1998, p. 861.*
Whalin et al., Molecular Pharmacology, 1991; 39(6): 711-717.*
Egawa et al., Japanese Journal of Pharmacology, 1997; 75:275-281.*
Merck Manuel, Home edition, 1997, pp. 12-15, 381-387, and 398-402.*
Stryer, L. Biochemistry, $4^{th}$ ed. W.H. Freeman and Company, New York, NY, 1995.
Kandel et al., Principles of Neural Science, $3^{rd}$ ed. Auflage, Elsevier, Kapietl, 1998, ch. 28, S. 403-408.
Martins, T., Mumby, M., Beavo, J., "Purification and Characterization of a Cyclic GMP-stimulated Cyclic Nucleotide Phosphosiesterase from Bovine Tissues", J. Biol Chem., 257:4, 1973-1979 (1982).
Yamamoto, T., Manganiello, V., Vaughan, M., "Purification and Characterization of a Cyclic GMP-stimulated Cyclic Nucleotide Phosphodiesterase from Calk Liver", J. Biol. Chem., 258: 20, 12526-12533 (1983).

(Continued)

*Primary Examiner*—San-Ming Hui

(57) ABSTRACT

The invention relates to the use of selective phosphodiesterase 2 (PDE 2) inhibitors for producing pharmaceuticals for improving perception, concentration, learning and/or memory.

2 Claims, 2 Drawing Sheets

OTHER PUBLICATIONS

Figure 1:
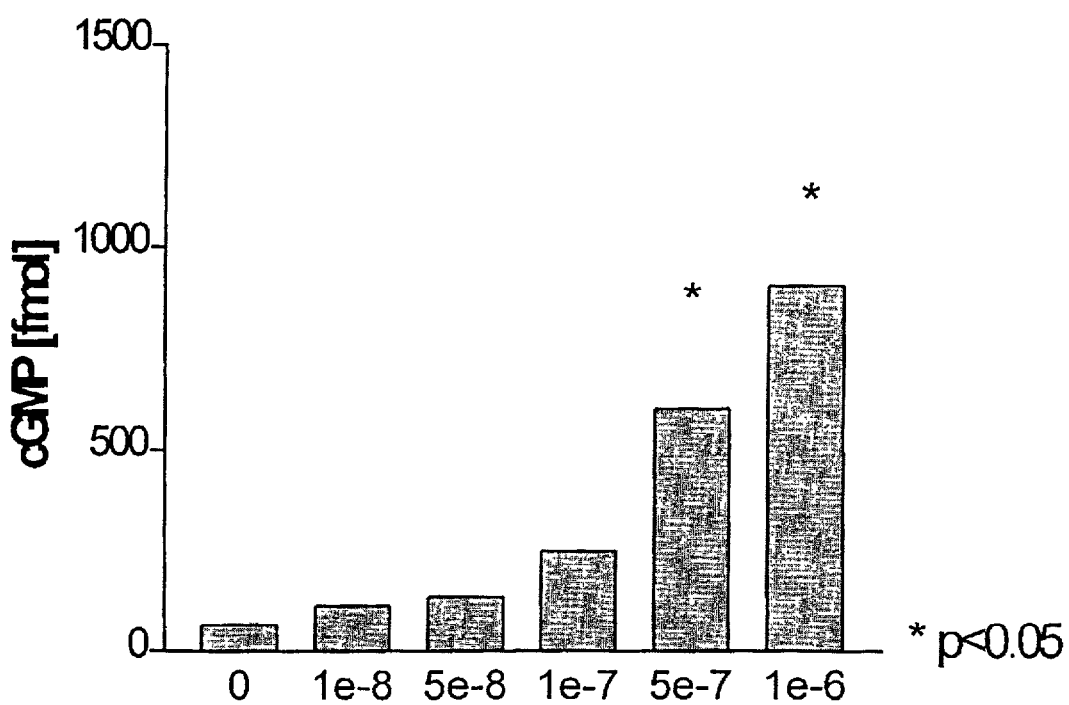

Grant, P., Mannarino, A., Colman, R., "Purification and Characterization of a Cyclic GMP-stimulated Cyclic Nucleotide Phosphodiesterase from the Cytosol of Human Platelets", Thrombosis Research, 59: 105-119 (1990).

Whalin, M., Strada, S., Thompson, W., "Purification and Partial Characterization of Membrane-associated Type II (cGMP-activatable) Cyclic Nucleotide Phosphodiesterase from Rabbit Brain" Biochim. Biophys. Acta., 972: 79-94 (1988).

Sonnenburg, W., Mullaney, P., Beavo, J., "Molecular Cloning of a Cyclic GMP-stimulated Cyclic Nucleotide Phosphodiesterase cDNA ", J. of Biol. Chem., 266: 26, 17655-17661 (1991).

Tanaka, T., Hockman, S., Moos, M., Taira, M., Meacci, E., Murashima, S., Manganiello, V., "Comparison of Putative cGMP-binding Regions in Bovine Brain and Cardiac cGMP-stimulated Phosphodiesterases", Second Messengers and Phosoproteins, 13: 87-98 (1991).

Rosman, G., Martins, T., Sonnenburg, W., Beavo, J., Ferguson, K., Loughney, K., "Isolation and Characterization of Human cDNAs Encoding a cGMP-stimulated 3', 5'-cyclic Nucleotide Phosphodiesterase". Gene, 191: 89-95 (1997).

* cited by examiner

SELECTIVE PDE 2 INHIBITORS AS PHARMACEUTICALS FOR IMPROVING PERCEPTION

The invention relates to the use of selective phosphodiesterase 2 (PDE 2) inhibitors for producing pharmaceuticals for improving perception, concentration, learning and/or memory.

Cellular activation of adenylate and guanylate cyclases respectively results in the cyclization of ATP and GTP to 5'-3' cyclic adenosine monophosphate (cAMP) and 5'-3' cyclic guanosine monophosphate (cGMP) respectively. These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG) (for a review: see Stryer, L., Biochemistry, 4th edition, Freeman, New York, 1995). Activated PKA and PKG are able in turn to phosphorylate a number of cellular effector proteins (for example ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (for a review: Kandel et al. in "Principles of Neural Science", 1991, 3rd edition, Elsevier, chapter 28, pp. 403–408.) The phosphodiesterases (PDE) are a control mechanism for controlling the activity of cAMP and cGMP and thus in turn these physiological processes. PDEs hydrolyse the cyclic monophosphates to the inactive monophosphates AMP and GMP. At least 21 PDE genes have now been described (*Exp. Opin. Investig. Drugs* 2000, 9, 1354–3784). These 21 PDE genes can be divided on the basis of their sequence homology into 11 PDE families (for proposed nomenclature, see: www.hs.washington.edu.). Individual PDE genes within a family are differentiated by letters (for example PDE1A and PDE1B). If different splice variants within a gene also occur, this is then indicated by an additional numbering after the letter (for example PDE1A1). The enzyme referred to originally as "cGMP-stimulated PDE" and later as PDE2 was biochemically isolated and purified for the first time from bovine hearts and bovine adrenal in 1982 (Martins et al. *J. Biol. Chem.* 1982, 257, 1973–1979). The particular feature of this phosphodiesterase is that it has positive cooperative kinetics in relation to the substrate cGMP. It has been postulated that small amounts of cGMP bind to the so-called cGMP-binding domain and thus bring about activation of the enzyme. This also increases the affinity of the catalytic domains for cGMP and cAMP (Martins et al. *J. Biol. Chem.* 1982, 257, 1973–1979). For this reason, PDE2 can hydrolyse and thus also control both second messenger systems through small amounts of cGMP.

PDEs stimulated by cGMP have also been described in various other tissues. These include, but are not confined to, the liver (Yamamoto et al. *J. Biol. Chem.* 1983, 258, 12526–12533.) and platelets (Grant et al. *Thromb Res.* 1990, 59, 105–119.). A membrane-bound form of cGMP-stimulated PDE has been isolated from rabbit brain (Whalin et al. *Biochim. Biophys. Acta.* 1988, 972, 79–94.). The cDNA of PDE2 was cloned for a first time from bovine and rat tissues (Sonnenburg et al. *J. Biol Chem.* 1991, 266, 17655–17661. Tanaka et al. *Second Messengers Phosphoproteins.* 1991, 13, 87–98.). Sonnenburg et al. also showed strong expression of the PDE2 mRNA in the cerebral cortex, the basal ganglia and the hippocampus. The sequence of the human isoform PDE2A3 sequence (GenBank Acc. No. U67733) was reported by Rosman et al. *Gene.* 1997, 191, 89–95. Of the tissues investigated therein, the detected expression of PDE2A was strong in brain and heart and weaker in liver, skeletal muscle, kidney and pancreas.

The only specific inhibitor of PDE2 described to date is erythro-9-(2-hydroxy-3-nonyl)adenine (EHNA: $IC_{50}=1$ μM). However, EHNA is also a very potent adenosine deaminase inhibitor ($IC_{50}=3$ nM), which means that cyto-biological and in vivo-pharmacological effects produced by EHNA cannot be interpreted unambiguously.

EP-A-0 771 799, WO 98/40384 and WO 00/12504 describe purinone, allopurinol and triazolopyrimidinone derivatives, their PDE-inhibitory effect and their suitability for the treatment of certain vascular disorders.

It has now been found, surprisingly, that selective PDE 2 inhibitors are suitable for producing pharmaceuticals for improving perception, concentration, learning or memory.

A PDE 2 inhibitor within the meaning of the invention is a compound which inhibits human PDE 2 under the conditions indicated below with an $IC_{50}$ of less than 10 μM, preferably less than 1 μM, particularly preferably less than 0.1 μM.

A selective PDE 2 inhibitor within the meaning of the invention is a compound which inhibits human PDE 2 under the conditions indicated below more strongly than the human cAMP PDEs 3B, 4B and 7B. It is preferred for $IC_{50}$ (PDE 2)/$IC_{50}$ (PDE 3B, 4B or 7B) to be less than 0.1.

The selective PDE 2 inhibitors are particularly suitable for improving perception, concentration, learning or memory after cognitive disturbances as occur in particular in situations/diseases/syndromes such as mild cognitive impairment, age-associated learning and memory disturbances, age-associated memory losses, vascular dementia, craniocerebral trauma, stroke, dementia occurring after strokes (post stroke dementia), post-traumatic craniocerebral trauma, general disturbances of concentration, disturbances of concentration in children with learning and memory problems, Alzheimer's disease, dementia with Lewy bodies, dementia with degeneration of the frontal lobes including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia with dementia or Korsakoff psychosis.

The invention preferably relates to the use according to the invention of PDE 2 inhibitors of the general formula (I),

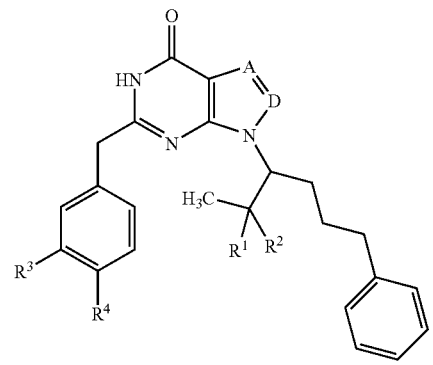

in which
A=D represents N=N, N=CH or $CR^5$=N, in which $R^5$ denotes hydrogen, methyl, ethyl or methoxy, $R^1$ and $R^2$ represent, together with the adjacent carbon atom, hydroxymethylene or carbonyl, and $R^3$ and $R^4$ represent independently of one another methyl, ethyl, methoxy, ethoxy or a radical of the formula $SO_2NR^6R^7$, in which $R^6$ and $R^7$ denote, independently of one another, hydrogen, $C_1$–$C_6$-alkyl, $C_3$–$C_7$-cycloalkyl, or $R^6$ and $R^7$ form, together with the adjacent nitrogen atom, an azetidin-1-yl, pyrrol-1-yl, piperid-1-yl, azepin-1-yl, 4-methylpiperazin-1-yl or morpholin-1-yl radical, or one of their salts.

$C_1$–$C_6$-Alkyl represents for the purpose of the invention a straight-chain or branched alkyl radical having 1 to 6 carbon atoms. A straight-chain or branched alkyl radical having 1 to 4 carbon atoms is preferred. Examples which may be mentioned are: methyl, ethyl, n-propyl, isopropyl, t-butyl, n-pentyl and n-hexyl.

$C_3$–$C_7$-Cycloalkyl represents for the purposes of the invention a cycloalkyl group having 3 to 7 carbon atoms. Those which may be mentioned as preferred are: cyclopropyl, cyclobutyl, cyclopentyl, cyclohexyl and cycloheptyl.

The substances according to the invention of the general formula (I) may also be in the form of salts. Physiologically acceptable salts are preferred for the purposes of the invention.

Physiologically acceptable salts may be salts of the compounds according to the invention with inorganic or organic acids. Preference is given to salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, benzene-sulphonic acid, toluenesulphonic acid or naphthalenedisulphonic acid.

Physiologically acceptable salts may likewise be metal or ammonium salts of the compounds according to the invention. Particular preference is given to alkali metal salts (for example sodium or potassium salts), alkaline earth metal salts (for example magnesium or calcium salts), and ammonium salts derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

The compounds of the general formula (I) are disclosed in EP-A-0 771 799, WO 98/40384 and WO 00/12504 or can be prepared by processes described therein. The disclosure of EP-A-0 771 799, of WO 98/40384 and of WO 00/12504 is incorporated herein by reference.

The active substance may act systemically and/or locally. For this purpose, it can be administered in a suitable way such as, for example, by the oral, parenteral, pulmonary, nasal, sublingual, lingual, buccal, rectal, transdermal, conjunctival or otic route, or as implant.

For these administration routes it is possible to administer the active substance in suitable administration forms.

Suitable for oral administration are known administration forms with fast and/or modified delivery of active substance, such as, for example, tablets (uncoated and coated tablets, for example enteric coatings), capsules, sugar-coated tablets, granules, pellets, powders, emulsions, suspensions and solutions.

Parenteral administration is possible with avoidance of an absorption step (intravenous, intraarterial, intracardiac, intraspinal or intralumbar route) or with inclusion of an absorption (intramuscular, subcutaneous, intracutaneous, percutaneous or intraperitoneal route). Administration forms suitable for parenteral administration are, inter alia, preparations for injection and infusion in the form of solutions, suspensions, emulsions, lyophilizates and sterile powders.

Suitable for the other administration routes are, for example, pharmaceutical forms for inhalation (inter alia powder inhalers, nebulizers), nasal drops/solutions, sprays; tablets or capsules for lingual, sublingual or buccal administration, suppositories, preparations for the ears and eyes, vaginal capsules, aqueous suspensions (lotions, shaking mixtures), lipophilic suspensions, ointments, creams, milk, pastes, dusting powders or implants.

The active substances can be converted in a manner known per se into the administration forms mentioned. This takes place with use of inert, non-toxic, pharmaceutically suitable excipients. These include, inter alia, carriers (for example microcrystalline cellulose), solvents (for example liquid polyethylene glycols), emulsifiers (for example sodium dodecyl sulphate), dispersants (for example polyvinylpyrrolidone), synthetic and natural biopolymers (for example albumin), stabilizers (for example antioxidants such as ascorbic acid), colouring materials (for example inorganic pigments such as iron oxides) or taste and/or odour masking agents.

In general, it has proved advantageous to administer amounts of about 0.001 to 30 mg/kg, preferably about 0.01 to 10 mg/kg, of body weight to achieve effective results on parenteral administration. The amount for oral administration is about 0.01 to 100 mg/kg, preferably about 0.1 to 30 mg/kg, of body weight.

It may nevertheless be necessary where appropriate to deviate from the stated amounts, in particular depending on the body weight, administration route, individual response to the active substance, type of preparation and time or interval over which administration takes place.

PDE Inhibition

The PDE 2 which can be stimulated by cGMP is isolated from bovine myocardium. The PDE 1 which can be stimulated by $Ca^{2+}$ calmodulin is isolated from porcine aorta, porcine brain or, preferably, from bovine aorta. The cGMP-specific PDE 5 is obtained from porcine small intestine, porcine aorta, human blood platelets and, preferably, from bovine aorta. Purification takes place by anion exchange chromatography on MonoQ$^R$ Pharmacia essential by the method of Hoey, M; Houslay, M. D., *Biochem. Pharmacol.* 1990, 40, 193–202 and Lugman et al. *Biochem. Pharmacol.* 1986, 35, 1743–1751.

The enzymatic activity is determined in an assay mixture of 100 µl in 20 mM Tris/HCl buffer pH 7.5 which contains 5 mM $MgCl_2$, 0.1 mg/ml bovine serum albumin and 800 Bq of either [$^3$H]-cAMP or [$^3$H]-cGMP. The final concentration of the respective nucleotides is $10^{-6}$ mol/l. The reaction is started by adding the enzyme, and the amount of enzyme is such that about 50% of the substrate are converted during the incubation time of 30 min. The substrate used for the assay of PDE 2 which can be stimulated by cGMP is [$^3$H]-cAMP, and $10^{-6}$ mol/l of unlabelled cGMP is added to the mixture. $CaCl_2$ 1 µM and calmodulin 0.1 µM are also added to the reaction mixture in order to assay the Ca-calmodulin-dependent PDE 1. The reaction is topped by adding 100 µl acetonitrile which contains 1 mM cAMP and 1 mM AMP. 100 µl of the reaction mixture are separated by HPLC, and the cleavage products are determined quantitatively on line using a flow scintillation counter. The substance concentration at which the reaction rate is reduced by 50% is measured. Also used for assays are the "Phosphodiesterase [$^3$H] cAMP-SPA enzyme assay" and the "Phosphodiesterase [$^3$H] cGMP-SPA enzyme assay" supplied by Amersham Life Science. The assay was carried out in accordance with the experimental protocol indicated by the manufacturer.

Human recombinant PDE2 (Rosman et al. *Gene* 1997 191, 89–95), PDE3B (Miki et al. *Genomics* 1996 36, 476–485), PDE4B (Bolger et al. *Mol. Cell. Biol.* 1993 13, 6558–6571) and PDE7B (Hetman et al. *Proc. Natl. Acad. Sci. U.S.A.* 2000 97, 472–476) are expressed in Sf9 cells with the aid of the pFASTBAC baculovirus expression system (Gibco BRL).

The activity of the test substances on human recombinant PDE2, PDE3B, PDE4B and PDE7B is determined using the [$^3$H]cAMP scintillation proximity assay (SPA) kit (TRKQ7090) from Amersham International (Little Chalfont, England) and on PDE1 and PDE5 using the [$^3$H]cGMP scintillation proximity assay (SPA) kit (TRKQ7100) from Amersham International (Little Chalfont, England).

Test substances are dissolved in 100% DMSO (10 mM), and this solution is diluted further with $H_2O$ (maximum final concentration in the assay: 10 µM). The PDE2 is prestimulated by adding cGMP (final concentration in the assay: $10^{-6}$ M). The enzyme is diluted in PDE buffer (20 mM TRIS/HCl, 5 mM $MgCl_2$, 0.1 mg/ml albumin, pH 7.5). The following volumes are pipetted into each well of a 96-well plate (Wallac, 1450-401): 10 µl of substance solution (10 µl of $H_2O$ for the 100% value), 10 µl of cGMP ($10^{-5}$ M), 70 µl of [$^3$H]-cAMP assay mixture (see kit), 10 µl of enzyme (no enzyme, instead +10 µl of $H_2O$ for the 0 value) to start the reaction. After incubation at 30° C. for 15 min, the reaction is stopped with 50 µl of SPA bead solution (see kit), and the plate is sealed with a film and shaken for 30 seconds. After the beads have settled out (about 15 min), the plate is measured in a beta counter.

Calmodulin $10^{-7}$ M and $CaCl_2$ 1 µM are added to the reaction mixture for the PDE1 measurement. PDE5 is measured using the [$^3$H] cGMP SPA assay. PDE3B, PDE4B and PDE7B are measured using the [$^3$H] cAMP scintillation proximity assay.

The exemplary embodiment 1 used, 6-(3,4-dimethoxybenzyl)-1-[1-(1-hydroxyethyl)-4-phenylbutyl)-3-methyl-1,5-dihydropyrazolo[3,4-d]pyrimidin-4-one, corresponds to Example 36 in WO 98/40384 and was prepared by the process described therein.

Inhibition of PDE isoenzymes by Example 1:

| Isoenzyme | Species | IC$_{50}$ [nM] |
| --- | --- | --- |
| PDE1 | bovine | 200 |
| PDE2 | bovine | 7 |
| PDE2 | human | 6 |
| PDE3B | human | >4000 |
| PDE4B | human | 2900 |
| PDE5 | human | 300 |
| PDE7B | human | 1600 |

Increasing the Intracellular Neuronal cGMP Concentration in Cell Cultures

PDE 2 inhibitors increase the intracellular neronal cGMP concentration after prestimulation of guanylate cyclase with $10^{-4}$ M sodium nitroprusside (SNP) in primary mouse brain cell cultures.

Mouse embryos were decapitated and the heads were transferred into dissection dishes. The scalp and roof of the skull were removed, and the exposed brains were transferred into another Petri dish. Using a binocular microscope and two forceps, the cerebrum (cortex) was isolated and cooled to 4° C. with ice. This dissection and the isolation of the cortical neurons were then carried out in accordance with a standard protocol with the papain dissociation system (Worthington Biochemical Corporation, Lakewood, N.J. 08701, USA) (Huettner et al. *J. Neurosci.* 1986, 6, 3044–3060.). The mechanically isolated neurons were cultivated at 150 000 cells/well in 200 µl of Neurobasal medium/well (Neurobasal; Gibco/BRL; 2 mM L-glutamine; in the presence of penicillin/streptomycin) in 96-well plates (pretreated with poly-D-lysine 100 µg/ml fir 20 min) under standard conditions (37° C., 5% $CO_2$) for 7 days. After 7 days, the medium was removed and the cells were washed with HBS buffer (Gibco/BRL). Then 100 µl of SNP solution and 100 µl of Example 1 (previously dissolved in 100% DMSO, 10 mM) in HBS were added to the cells so that the final concentration of SNP was 100 mM and that of Example 1 was as indicated in FIG. 1, and incubated at 37° C. for 20 min. The cells were then lysed with 200 µl lysis buffer (cGMP kit code RPN 226; from Amersham Pharmacia Biotech.) and cGMP concentration was measured as stated by the manufacturer. All the measurements were carried out in triplicate. The statistical analysis took placing using Prism Software Version 2.0 (GraphPad Software Inc., San Diego, Calif. USA).

On parallel incubation of neurons with SNP (a guanylate cyclase stimulator) and Example 1 even at a concentration of 100 nM there was found to be distinct increase in the intracellular cGMP level (FIG. 1).

FIG. 1: Intracellular cGMP concentration in primary mouse (E18) cortex cultures (ordinate) after treatment with SNP and Example 1 (abscissa)

Cells were treated with 100 mM SNP (0) or with 100 mM SNP and Example 1 ($1\times10^{-8}$ M; $5\times10^{-8}$ M; $1\times10^{-7}$ M; $5\times10^{-7}$ M; $1\times10^{-6}$ M) for 20 min. The intracellular cGMP level was then measured.

Object Recognition Test

The object recognition test is a memory test. It measures the ability of rats (and mice) to distinguish between familiar and unfamiliar objects.

The test was carried out as described (Blokland et al. *NeuroReport* 1998, 9, 4205–4208; Ennaceur, A., Delacour, J., *Behav. Brain Res.* 1988, 31, 47–59; Ennaceur, A., Meliani, K., *Psychopharmacology* 1992, 109, 321–330; Prickaerts, et al. *Eur. J. Pharmacol.* 1997, 337, 125–136).

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect will lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object longer than the old one; that is to say the rat has recognized the old object.

Figure 2:
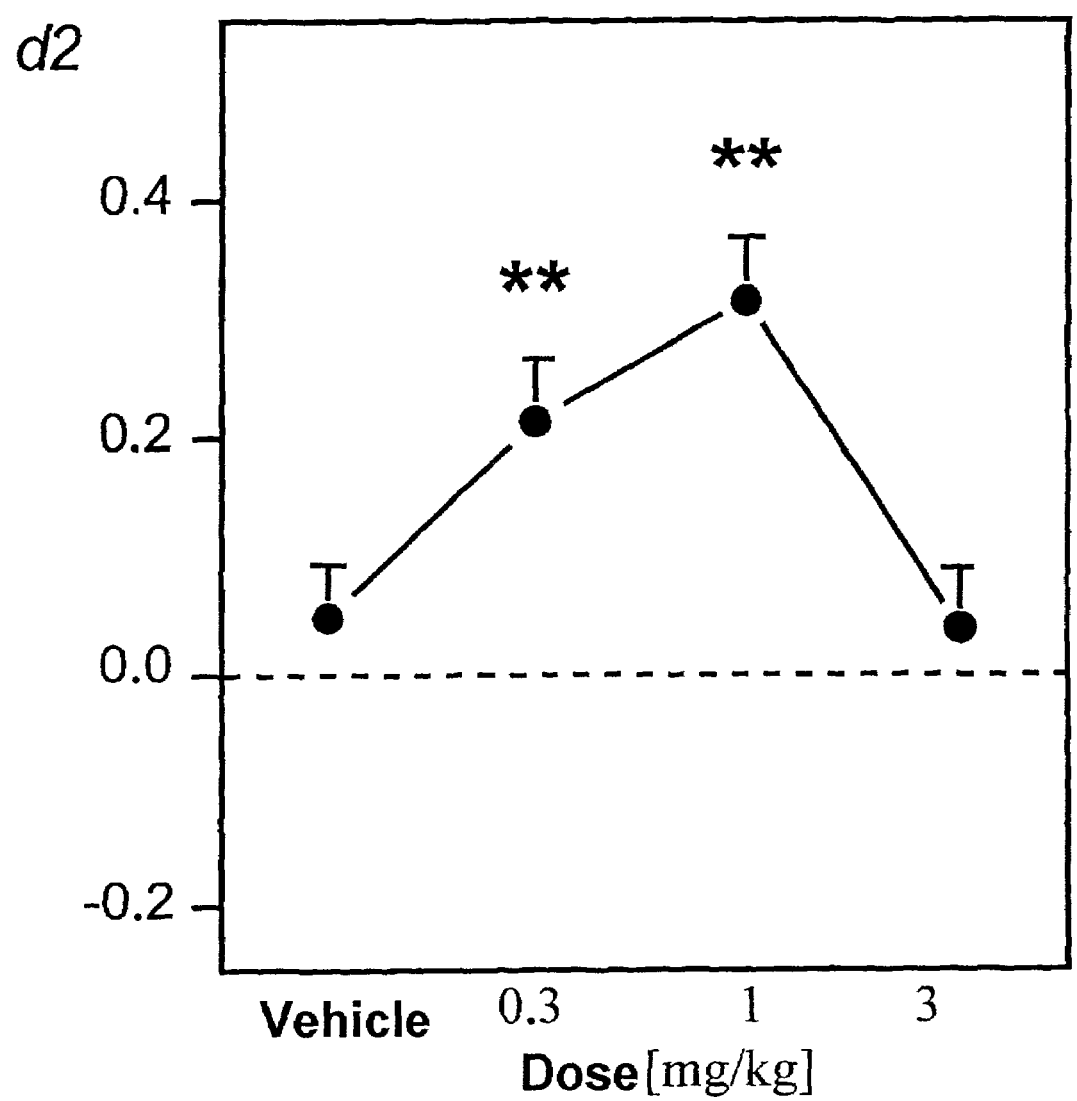

The effects of Example 1 on object recognition by rats 24 hours after the first run were investigated. The animals received Tylose alone, or Example 1 in dosages of 0.3, 1.0 or 3.0 mg/kg of body weight suspended in Tylose, orally, immediately following the first run with two identical objects. This was followed 24 hours later by the second run in each case. After a washout period of 2 or 3 days, a new dosage of Example 1 was tested in the same rats, until the memory capacity of all the rats had been measured twice with all the dosages. Thus, all the animals served as their own controls. The results of this study are shown in FIG. 2. Surprisingly, the memory capacity was improved in the second run after treatment with 0.3 and 1.0 mg/kg of Example 1 compared with the control condition (treatment with Tylose alone). The discrimination index was greater than zero and differed from the discrimination index achieved with the control condition.

The results of this test are depicted in FIG. 2:

FIG. 2: Effect of Example 1 on the discrimination index (d2) in the object recognition test (averages+SEM). Vehicle treatment was with 1% Tylose. The animals treated with the substance were treated with 0.3 mg/kg, 1 mg/kg and 3 mg/kg. Statistical analysis: **P<0.01.

The invention claimed is:

1. A method for treating a disorder of perception, concentration, learning and/or memory, where said disorder of perception, concentration, learning and/or memory is a result of Alzheimer's disease, comprising administering to a mammal in need of such treatment an effective amount of a selective PDE 2 inhibitor which inhibits human PDE 2 more strongly than it inhibits the human cAMP PDEs 3B, 4B and 7B, and which has the general formula (I)

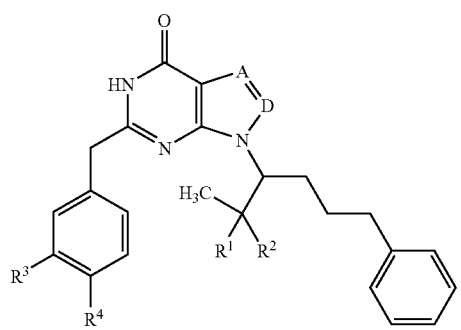

(I)

wherein
A=D represents N=N, N=CH or $CR^5$=N, in which $R^5$ denotes hydrogen, methyl, ethyl or methoxy,
$R^1$ and $R^2$ represent, together with the adjacent carbon atom, hydroxymethylene or carbonyl, and
$R^3$ and $R^4$ represent independently of one another methyl, ethyl, methoxy, ethoxy or a radical of the formula $SO_2NR^6R^7$,
in which
$R^6$ and $R^7$ denote, independently of one another, hydrogen, $C_1$–$C_6$-alkyl, $C_3$–$C_7$-cycloalkyl, or
$R^6$ and $R^7$ form, together with the adjacent nitrogen atom, an azetidin-1-yl, pyrrol-1-yl, piperid-1-yl, azepin-1-yl, 4-methylpiperazin-1-yl or morpholin-1-yl radical,
or a pharmaceutically acceptable salt thereof.

2. A method for treating a disorder of perception, concentration, learning and/or memory, where said disorder of perception, concentration, learning and/or memory is a result of Parkinson's disease, comprising administering to a mammal in need of such treatment an effective amount of a selective PDE 2 inhibitor which inhibits human PDE 2 more strongly than it inhibits the human cAMP PDEs 3B, 4B and 7B, and which has the general formula (I)

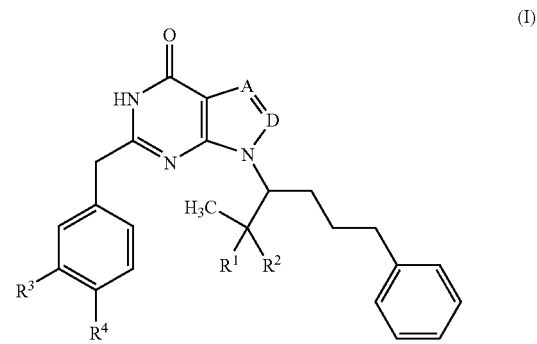

(I)

wherein
A=D represents N=N, N=CH or $CR^5$=N, in which $R^5$ denotes hydrogen, methyl, ethyl or methoxy,
$R^1$ and $R^2$ represent, together with the adjacent carbon atom, hydroxymethylene or carbonyl, and
$R^3$ and $R^4$ represent independently of one another methyl, ethyl, methoxy, ethoxy or a radical of the formula $SO_2NR^6R^7$,
in which
$R^6$ and $R^7$ denote, independently of one another, hydrogen, $C_1$–$C_6$-alkyl, $C_3$–$C_7$-cycloalkyl, or
$R^6$ and $R^7$ form, together with the adjacent nitrogen atom, an azetidin-1-yl, pyrrol-1-yl, piperid-1-yl, azepin-1-yl, 4-methylpiperazin-1-yl or morpholin-1-yl radical,
or a pharmaceutically acceptable salt thereof.

* * * * *